(12) United States Patent
Hand et al.

(10) Patent No.: US 10,682,343 B2
(45) Date of Patent: *Jun. 16, 2020

(54) SNORING TREATMENT (71) Applicants: James M. Hand, Collegeville, PA (US); Linda M. Hand, Collegeville, PA (US)

(72) Inventors: James M. Hand, Collegeville, PA (US); Linda M. Hand, Collegeville, PA (US)

(*) Notice: Subject to any disclaimer, the term of this patent is extended or adjusted under 35 U.S.C. 154(b) by 197 days.

This patent is subject to a terminal disclaimer.

(21) Appl. No.: 15/429,931

(22) Filed: Feb. 10, 2017

(65) Prior Publication Data
US 2017/0151222 A1 Jun. 1, 2017

Related U.S. Application Data (63) Continuation of application No. 14/211,278, filed on Mar. 14, 2014.

(60) Provisional application No. 61/788,958, filed on Mar. 15, 2013.

(51) Int. Cl.
| | |
|---|---|
| *A61K 31/4402* | (2006.01) |
| *A23L 33/10* | (2016.01) |
| *A23L 33/00* | (2016.01) |
| *A61K 9/00* | (2006.01) |
| *A61K 9/48* | (2006.01) |
| *A61K 31/135* | (2006.01) |
| *A61K 31/4045* | (2006.01) |
| *A61K 31/405* | (2006.01) |
| *A61K 45/06* | (2006.01) |

(52) U.S. Cl.
CPC .......... *A61K 31/4402* (2013.01); *A23L 33/10* (2016.08); *A23L 33/40* (2016.08); *A61K 9/0053* (2013.01); *A61K 9/4825* (2013.01); *A61K 31/135* (2013.01); *A61K 31/405* (2013.01); *A61K 31/4045* (2013.01); *A61K 45/06* (2013.01); *A23V 2002/00* (2013.01)

(58) Field of Classification Search
CPC .................................................. A61K 31/4402
See application file for complete search history.

(56) References Cited

U.S. PATENT DOCUMENTS

| | | | |
|---|---|---|---|
| 6,034,117 A | 3/2000 | Hedner et al. | |
| 8,071,073 B2* | 12/2011 | Dang | A61K 9/0043 424/45 |

FOREIGN PATENT DOCUMENTS

| | | |
|---|---|---|
| WO | 199851309 | 11/1998 |
| WO | 2012170883 | 12/2012 |
| WO | 2014138162 | 9/2014 |

OTHER PUBLICATIONS

Hartmann, E, Effects of L-tryptophan on sleepiness and on sleep, 1983, J Psychiatr Res, 17(2), pp. 107-113, abs (Year: 1983).*

* cited by examiner

*Primary Examiner* — Jeffrey S Lundgren
*Assistant Examiner* — Tori Strong
(74) *Attorney, Agent, or Firm* — Duane Morris LLP (57) ABSTRACT

The present invention features compositions and methods for treatment of snoring. We describe compositions comprising an antihistamine or a pharmaceutically acceptable salt thereof and one or more dietary supplements or pharmaceutically acceptable salts thereof. The compositions can be administered to a subject suffering from snoring.

31 Claims, 2 Drawing Sheets diphenhydramine doxylamine

FIG. 1

FIG. 2

SNORING TREATMENT

CROSS-REFERENCE TO RELATED APPLICATIONS

This application is a Continuation of U.S. application Ser. No. 14/211,278, filed Mar. 14, 2014, which claims the benefit of the filing date of U.S. Provisional Application No. 61/788,958 which was filed Mar. 15, 2013. The entire content of these applications is hereby incorporated by reference herein.

FIELD OF THE INVENTION

This invention relates to methods and compositions useful for the treatment of sleep disordered breathing, and more particularly to methods for reducing or attenuating snoring.

BACKGROUND

Snoring is one of the most common forms of sleep disordered breathing. Snoring occurs if the flow of air through the mouth and nose becomes obstructed during sleep, resulting in audible vibration of the soft palate and other structures in the mouth and throat. The prevalence of snoring varies widely among different populations, with estimates ranging from 5 to 86% in the adult males and about 2 to 59% in adult females. Chronic snoring is reported to affect about 40% of adult men and 20% of adult women. Risk factors for snoring include increasing age, obesity, weight gain, body posture, retrognathia, nasal blockage, asthma, alcohol consumption, smoking, and the use of muscle relaxants.

Snoring can have serious health and social consequences. Many people who snore complain of tiredness on waking, excessive sleepiness during the day, poor work performance, and difficulty with concentration. Habitual loud snoring may also significantly impair the sleep quality of the bed partner and/or other members of the snorer's household. Methods of treatment can include lifestyle modifications, nasal decongestants, and devices such as tongue-retaining devices, mandibular advancement appliances and application of continuous positive airway pressure (CPAP) via a nasal mask. Although the CPAP device is very effective in eliminating snoring in chronic sleep apnea, the nasal mask can be difficult to tolerate and non-apneic snorers tend to be reluctant to commit to long-term use. Surgical remedies are generally reserved only for patients with obvious anatomic abnormalities such as nasal or pharyngeal obstruction. Surgery does not generally provide complete resolution of snoring, although it does improve breathing and allow patients to better tolerate other therapies such as nasal CPAP. There is a continuing need for effective, non-invasive therapies to reduce or eliminate snoring.

SUMMARY

The present invention is based in part on our discovery that compositions comprising an antihistamine and a dietary supplement were effective in reducing snoring. Accordingly, the present invention features methods and compositions that can be used to treat snoring. The methods and composition are applicable to snoring that can stem from any of a wide range of medical conditions that result in the persistent or recurring sleep disordered breathing, for example, anatomical disorders, obesity, excess alcohol or food consumption prior to bedtime, and chronic nasal congestion. The methods of the invention can encompass treating a subject having these conditions. Regardless of whether the snoring results from a particular cause, the methods can be carried out by administering to a subject (e.g., a human patient) in need of treatment a pharmaceutically acceptable composition comprising an antihistamine or a pharmaceutically acceptable salt thereof and a dietary supplement or a pharmaceutically acceptable salt thereof. The antihistamine and the dietary supplement can be formulated in various ways and can include pharmaceutically acceptable carriers. For ease of reading, we will not repeat the phrase "or a pharmaceutically acceptable salt thereof" on every occasion. It is to be understood that where an antihistamine and a dietary supplement can be used, a pharmaceutically acceptable salt of the antihistamine and a dietary supplement may also be used.

Accordingly, the invention features physiologically acceptable compositions of an antihistamine and a dietary supplement and methods by which the compositions can be administered to a subject diagnosed as having sleep disordered breathing, for example, snoring. These methods can include the steps of a) identifying a subject (e.g., a human patient) who is in need of treatment for snoring; and b) providing to the subject a therapeutically effective amount of a pharmaceutical composition including an antihistamine and a dietary supplement. The pharmaceutical composition can result in a reduction or attenuation of the intensity, duration or loudness of snoring. We may use the terms "subject," "individual" and "patient" interchangeably. While the present methods are certainly intended for application to human patients, the invention is not so limited. Domesticated animals, including, for example, cats, dogs, horses, cows and other domesticated animals can also be treated.

Figure 1:
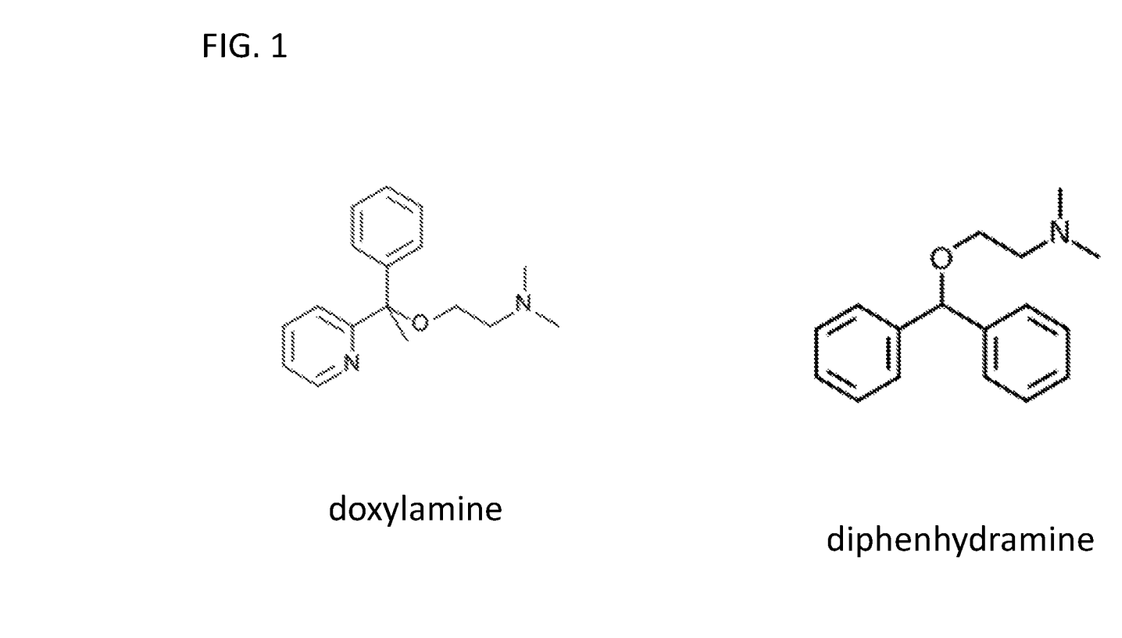
FIG. 1 depicts the structures of exemplary sedating antihistamines.
Figure 2:
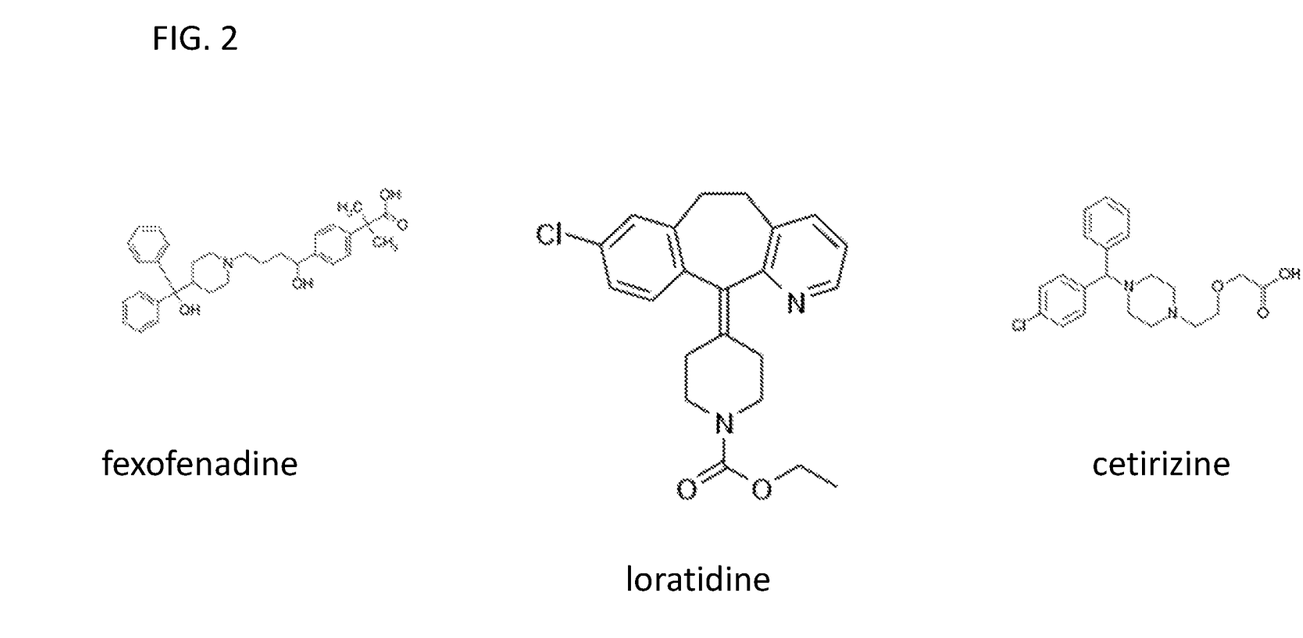
FIG. 2 depicts the structures of exemplary non-sedating antihistamines.

The pharmaceutically acceptable compositions of the invention include an antihistamine or pharmaceutically acceptable salt thereof. The antihistamine can be a sedating antihistamine or a non-sedating antihistamine. Exemplary sedating antihistamines include doxylamine ((RS)-N,N-dimethyl-2-(1-phenyl-1-pyridin-2-yl-ethoxy)-ethanamine) and diphenhydramine (2-(diphenylmethoxy)-N,N-dimethylethanamine); exemplary non-sedating antihistamines include cetirizine ((±)-[2-[4-[(4-chlorophenyl)phenylmethyl]-1-piperazinyl]ethoxy]acetic acid), loratidine (Ethyl 4-(8-chloro-5,6-dihydro-11H-benzo[5,6]cyclohepta[1,2-b]pyridin-11-ylidene)-1-piperidinecarboxylate) and fexofenadine (RS)-2-[4-[1-Hydroxy-4-[4-(hydroxy-diphenylmethyl)-1-piperidyl]butyl]phenyl]-2-methyl-propanoic acid). Structures of exemplary sedating anti-histamines are shown in FIG. 1; structures of exemplary non-sedating antihistamines are shown in FIG. 2. The compositions also include one or more dietary supplements. The dietary supplement can be an indole-based supplement, for example, L-tryptophan, 5-hydroxytryptophan, serotonin, N-acetyl-5-hydroxytryptamine or melatonin, or a metabolite of L-tryptophan, 5-hydroxytryptophan, serotonin, N-acetyl-5-hydroxytryptamine or melatonin. In some embodiments, the compositions can exclude a serotonin re-uptake inhibitor or a selective serotonin re-uptake inhibitor.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Suitable pharmaceutically acceptable salts can include, for example, succinate salts, hydrochloride or citrate salts. The invention is not so limited however and lists of exemplary salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. It will also be understood that certain compounds of the present invention may exist in solvated, for example hydrated, as well as unsolvated forms. It will further be understood that the present invention encompasses all such solvated forms.

The composition comprising an antihistamine and a dietary supplement is administered for a time and in an amount sufficient to reduce or attenuate snoring. Choice of specific clinical endpoints may depend, in part, upon the nature of the underlying medical condition that contributes to snoring. The dosage may vary, but in general the subject can receive from about 0.001 g to about 0.20 g of antihistamine per unit dose, and about 0.001 g to about 1.0 g of tryptophan per unit dose. In some embodiments the compositions can include an additional dietary supplement, for example melatonin and 0.0001 g to about 0.01 g per unit dose. The frequency of treatment may also vary, e.g., one or more times per day or every so-many hours.

The compositions can be administered to a subject in a variety of ways. For example, the compositions can be administered by one or more of the by one or more of the following routes of administration: oral, buccal, sublingual, sublabial, nasal inhalation, urogenital, intravesicular, intravaginal, rectal, transdermal, subcutaneous, intravenous, or intramuscular. The treatment regime can vary depending upon various factors typically considered by one of ordinary skill in the art. These factors include the route of administration, the nature of the formulation, the subject's size, weight, surface area, age, gender, other drugs being administered to the patient, the patient's perception, and the judgment of any attending physician. The compositions can be administered along with or in addition to other treatments for snoring e.g., lifestyle modifications, nasal decongestants, oral appliances, CPAP via a nasal mask, and surgical treatments.

The methods of the invention are applicable to a wide range of conditions that result in sleep disordered breathing and for which symptomatic relief from snoring is desired. These include "simple" snoring. e.g., snoring that is unaccompanied by apneas or hypopnea during sleep. The methods are not so limited and can be used to provide symptomatic relief in more serious disorders such as upper airway resistance syndrome (UARS), and obstructive sleep apnea-hypopnea syndrome (OSAHS) where the primary treatment is insufficient to completely resolve snoring.

Provided herein is a method of reducing snoring in a subject, the method comprising: (a) identifying a subject who is in need of treatment for snoring; and (b) administering to the subject a therapeutically effective amount of pharmaceutical composition comprising an antihistamine and one or more dietary supplements. The composition can be administered by one or more of the following routes of administration: oral, buccal, sublingual, sublabial, nasal inhalation, urogenital, intravesicular, intravaginal, rectal, transdermal, subcutaneous, intravenous, or intramuscular. Oral administration can include administering a capsule or tablet dosage form one or more times per day. In some embodiments, the anti-histamine is a sedating antihistamine, for example, doxylamine or diphenhydramine. In some embodiments, the antihistamine is a non-sedating antihistamine, for example cetirizine, loratidine or fexofenadine. The dietary supplement can include L-tryptophan, 5-hydroxytryptophan, serotonin, N-acetyl-5-hydroxytryptamine or melatonin or a metabolite thereof. The pharmaceutical composition can also include one or more of a vitamin, mineral, a pharmaceutically acceptable salt, and a pharmaceutical carrier. In some embodiments, the composition comprises doxylamine, L-tryptophan, and melatonin.

Also provided is a method of treating a subject who is suffering from snoring, the method comprising: a) identifying a subject in need of treatment; and b) administering to the subject a therapeutically effective amount of a pharmaceutical composition comprising an antihistamine and a dietary supplement. The composition can be administered by one or more of the following routes of administration: oral, buccal, sublingual, sublabial, nasal inhalation, urogenital, intravesicular, intravaginal, rectal, transdermal, subcutaneous, intravenous, or intramuscular. Oral administration can include administering a capsule or tablet dosage form one or more times per day. In some embodiments, the anti-histamine is a sedating antihistamine, for example, doxylamine or diphenhydramine. In some embodiments, the anti-histamine is a non-sedating antihistamine, for example cetirizine, loratidine or fexofenadine. The dietary supplement can include L-tryptophan, 5-hydroxytryptophan, serotonin, N-acetyl-5-hydroxytryptamine or melatonin or a metabolite thereof. The pharmaceutical composition can also include one or more of a vitamin, mineral, a pharmaceutically acceptable salt, and a pharmaceutical carrier. In some embodiments, the composition comprises doxylamine, L-tryptophan, and melatonin.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. The details of one or more embodiments of the invention are set forth in the accompanying drawings and the description below. Other features, objects, and advantages of the invention will be apparent from the description and drawings, and from the claims.

DETAILED DESCRIPTION

We further describe below the present methods for treatment of snoring. These methods can be applied to, and are expected to benefit subjects having any of a variety of medical conditions that can give rise to snoring. The methods are based, inter alia, on the inventor's discovery that administration of a pharmaceutical composition comprising an antihistamine and a dietary supplement resulted in a reduction in snoring.

Snoring is an atypical condition in that it is not always recognized by the snorer himself. It is often the snorer's bed partner, whose own sleep is disrupted due to snoring, that prompts a snorer to seek symptomatic relief. The International Classification of Sleep Disorders: Diagnostic and Coding Manual defines snoring (ICSD 786.09) as "respiratory sound generated in the upper airway during sleep that typically occurs during inspiration but may also occur in expiration, without episodes of apnea or hypoventilation." Snoring is a result of the alterations in the configuration and properties of the upper airway (from the nasopharynx to the laryngopharynx) that occur during sleep. Any membranous portion of the airway that lacks cartilaginous support, including the soft palate, uvula, and the pharyngeal walls, can produce the harsh breathing sounds typically recognized as snoring. Snoring is usually an inspiratory sound, but it can also occur in expiration. Snoring is most common during stages 2, 3, and 4 of sleep because airway elastance and muscle tone due to sympathetic activity and neural output to the upper airway walls are different during rapid eye movement (REM) and non-REM sleep.

While we believe we understand certain events that occur upon administration of compositions comprising an antihistamine and a dietary supplement, the compositions of the present invention are not limited to those that work by affecting any particular cellular mechanism. Our working hypothesis is that compositions comprising an antihistamine and a dietary supplement may reduce snoring via beneficial effects on upper airway muscle activity or neural tone.

Compositions

The compositions described herein include an antihistamine and a dietary supplement. The antihistamine can be a sedating or nonsedating antihistamine (i.e., an $H_1$ receptor antagonist) for example doxylamine or diphenhydramine or fexofenadine or loratidine or cetirizine or a prodrug or active metabolite thereof. In some embodiments, the antihistamine can be a combination of two or more different antihistamines. Exemplary combinations include combinations of sedating antihistamines, e.g., doxylamine and diphenhydramine; combinations of non-sedating antihistamines, e.g., fexofenadine and/or loratidine and/or cetirizine; and combinations of a sedating and a non-sedating antihistamine, e.g., doxylamine plus fexofenadine and/or loratidine and/or cetirizine; or diphenhydramine plus fexofenadine and/or loratidine and/or cetirizine.

The compositions also include one or more dietary supplements. The dietary supplement can be an indole-based supplement, for example, L-tryptophan, 5-hydroxytryptophan, serotonin, N-acetyl-5-hydroxytryptamine or melatonin, or a metabolite of L-tryptophan, 5-hydroxytryptophan, serotonin, N-acetyl-5-hydroxytryptamine or melatonin. The dietary supplement can include any combination of L-tryptophan, 5-hydroxytryptophan, serotonin, N-acetyl-5-hydroxytryptamine or melatonin, or a metabolite of L-tryptophan, 5-hydroxytryptophan, serotonin, N-acetyl-5-hydroxytryptamine and melatonin, for example, L-tryptophan and melatonin, L-tryptophan and serotonin, L-tryptophan and 5-hydroxytryptophan, L-tryptophan and N-acetyl-5-hydroxytryptamine. In some embodiments, the composition can exclude one or more of L-tryptophan, 5-hydroxytryptophan, serotonin, N-acetyl-5 hydroxytryptamine or melatonin, or a metabolite of L-tryptophan, 5-hydroxytryptophan, serotonin, N-acetyl-5-hydroxytryptamine or melatonin. In some embodiments, the compositions can include or exclude one or more vitamins, e.g., vitamin $B_3$ or $B_6$. In some embodiments, the compositions can include or exclude one or more minerals, e.g., calcium or magnesium.

The compounds described herein, including those conforming to any formula, can be asymmetric (e.g., having one or more stereocenters). All stereoisomers, such as enantiomers and diastereomers, are intended unless otherwise indicated. The present compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated for the present compounds. Cis and trans geometric isomers of the present compounds are described and may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include ketone-enol pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediate or final compounds. Isotopes include those atoms having the same atomic number but different mass numbers. For example, isotopes of hydrogen include tritium and deuterium.

The term, "compound," as used with respect to any compound described herein, is meant to include all stereoisomers, geometric isomers, tautomers, and isotopes of the structures depicted. All compounds, and pharmaceutically acceptable salts thereof, are also meant to include solvated or hydrated forms.

The compounds of the present invention can be prepared in a variety of ways known to one of ordinary skill in the art of organic synthesis. The compounds of the present invention can be synthesized using standard methods, together with synthetic methods known in the art of synthetic organic chemistry or variations thereon as appreciated by one of ordinary skill in the art.

The compounds can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art. The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. In general, "pharmaceutically acceptable salts" refer to derivatives of the disclosed compounds wherein the parent compound is modified by converting an existing acid or base moiety to its salt form. "Pharmaceutically acceptable" generally encompasses those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and Journal of Pharmaceutical Science, 66, 2 (1977), each of which is incorporated herein by reference in its entirety.

As described above, the compounds of the present invention can be prepared in a variety of ways known to one of ordinary skill in the art of chemical synthesis. The present compounds can be prepared from readily available starting materials using the following general methods and procedures. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one of ordinary skill in the art by routine optimization procedures.

Regardless of their original source or the manner in which they are obtained, the compounds of the invention can be formulated in accordance with their use. For example, the compounds can be formulated within compositions for administration to a patient. When employed as pharmaceuticals, any of the present compounds can be administered in the form of pharmaceutical compositions. The compositions can include or exclude an excipient. These compositions can be prepared in a manner well known in the pharmaceutical art, and can be administered by a variety of routes, depending upon whether local or systemic treatment is desired and upon the area to be treated. Administration may be oral, parenteral, topical (including skin, ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include or exclude transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, one or more of the compounds described herein in combination with one or more pharmaceutically acceptable carriers. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. As is known in the art, the type of diluent can vary depending upon the intended route of administration. The resulting compositions can include or exclude additional agents, such as preservatives. The compounds may also be applied to a surface of a device (e.g., a catheter) or contained within a pump, patch, or other drug delivery device. The compounds of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well-known reference text in this field, and in the USP/NF (United States Pharmacopeia and the National Formulary). In preparing a formulation, the active compound can be milled to provide the appropriate particle size prior to combining with the other ingredients. If the active compound is substantially water insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The compositions can include or exclude lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include or exclude: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above.

The amount of antihistamine per dose can vary depending upon the specific antihistamine that is used. For example a subject may receive from 0.001 g to 0.20 g per unit dose of an antihistamine. More specifically, a subject can receive about 0.001 g per unit dose; about 0.002 g per unit dose; about 0.005 g per unit dose; about 0.010 g per unit dose; about 0.0125 g per unit dose about 0.015 g per unit dose; about 0.020 g per unit dose; about 0.025 g per unit dose; about 0.030 g per unit dose; about 0.035 g per unit dose; about 0.040 g per unit dose; about 0.045 g per unit dose; about 0.050 g per unit dose; about 0.060 g per unit dose; about 0.070 g per unit dose; about 0.075 g per unit dose; about 0.080 g per unit dose; about 0.090 g per unit dose; about 0.100 g per unit dose; about 0.125 g per unit dose; about 0.150 g per unit dose; about 0.180 g per unit dose; or about 0.200 g per unit dose. In general, dosages for sedating antihistamines, e.g., doxylamine and diphenhydramine, will be from about 0.001 to about 0.050 g to about 0.1 g per unit dose. In general, dosages for non-sedating antihistamines, e.g., fexofenadine or loratidine or cetirizine, will be from about 0.001 to about 0.200 g per unit dose.

Similarly, the amount of the dietary supplement can also vary. For example, when the dietary supplement is tryptophan the subject can receive about 0.001 g to about 1.0 g of L-tryptophan per unit dose. More specifically, the subject can receive about 0.001 g per unit dose; about 0.002 g per unit dose; about 0.05 g per unit dose; about 0.15 g per unit dose; about 0.2 g per unit dose; about 0.25 g per unit dose; about 0.3 g per unit dose; about 0.325 g per unit dose; about 0.4 g per unit dose; about 0.45 g per unit dose; about 0.50 g per unit dose. When the dietary supplement is melatonin, the subject can receive about 0.0001 g to about 0.01 g of melatonin per unit dose. More specifically, the subject can receive about 0.0001 g per unit dose; about 0.0002 g per unit dose; about 0.0005 g per unit dose; about 0.001 g per unit dose; about 0.0015 g per unit dose; about 0.002 g per unit dose; about 0.003 g per unit dose; about 0.005 g per unit dose; about 0.007 g per unit dose; about 0.008 g per unit dose; about 0.001 g per unit dose.

In some embodiments, the formulation can include about 0.001 g per unit dose to 0.05 g per unit dose of a sedating antihistamine, e.g., doxylamine or diphenhydramine and about 0.001 g per unit dose to about 1.0 g per unit dose of tryptophan and about 0.0001 g per unit dose to about 0.01 g per unit dose of melatonin. More specifically, in some embodiments, the formulation can include 0.0125 g per unit dose of doxylamine, 0.325 g per unit dose of L-tryptophan and 0.0015 g per unit dose of melatonin. In some embodiments, the formulation can include 0.080 g per unit dose of doxylamine, 0.300 g per unit dose of L-tryptophan and 0.0015 g per unit dose of melatonin. In some embodiments, the formulation can include about 0.001 g per unit dose to 0.20 g per unit dose of a non-sedating antihistamine, e.g., fexofenadine or loratidine or cetirizine and about 0.001 g per unit dose to about 1.0 g per unit dose of tryptophan and about 0.0001 g per unit dose to about 0.01 g per unit dose of melatonin. More specifically, in some embodiments, the formulation can include 0.180 g fexofenadine, 0.325 g L-tryptophan and 0.0015 g melatonin per unit dose.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/or known in the art. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner. The compositions administered to a patient can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations typically will be between about 3 and 11, for example, between about 5 to 9, between 6 and 7, between 7 and 8. It will be understood that use of certain of the foregoing excipients, carriers, or stabilizers could result in the formation of pharmaceutical salts.

The therapeutic dosage of the compounds of the present invention can vary according to, for example, the particular use for which the treatment is made, the manner of administration of the compound, the health and condition of the patient, and the judgment of the attending clinician. The proportion or concentration of a compound of the invention in a pharmaceutical composition can vary depending upon a number of factors including dosage, chemical characteristics (e.g., hydrophobicity), and the route of administration. Some typical dose ranges are from about 1 µg/kg to about 1 g/kg of body weight per day. The dosage is likely to depend on such variables as frequency and severity of snoring, the overall health status of the particular patient, the relative biological efficacy of the compound selected, formulation of the excipient, and its route of administration. Effective doses can be extrapolated from dose-response curves derived from in vitro or animal model test systems.

Methods of Treatment

The compositions disclosed herein are generally and variously useful for treatment of snoring. A patient is effectively treated whenever a clinically beneficial result ensues. This may mean, for example, a complete resolution of snoring, a decrease in the severity of snoring, for example, the intensity or loudness of snoring, or a decrease in the frequency of snoring. These methods can further include the steps of a) identifying a subject who snores; and b) providing to the subject a therapeutically effective amount of a composition comprising an antihistamine and one or more dietary supplements as described herein. Any method can be used to identify a subject who snores, including subjective methods (e.g., reporting by a bed partner or family member or by the snorer him or herself) or clinical analysis based on questionnaires, airway examination, a sound recording device or polysomnography. An amount of such a composition provided to the subject that reduces snoring, i.e., results in a complete resolution of snoring, a decrease in the severity of snoring, a decrease in the intensity of snoring, or a decrease in the frequency of snoring is considered a therapeutically effective amount. The present methods may also include a monitoring step to help optimize dosing and scheduling as well as predict outcome.

The methods disclosed herein can be applied to a wide range of species, e.g., humans, non-human primates (e.g., monkeys), horses or other livestock, dogs, cats, ferrets or other mammals kept as pets, rats, mice, or other laboratory animals.

The methods of the invention can be expressed in terms of the preparation of a medicament. Accordingly, the invention encompasses the use of the agents and compositions described herein in the preparation of a medicament. The compounds described herein are useful in therapeutic compositions and regimens or for the manufacture of a medicament for use in treatment of snoring.

The dosage required will depend on the route of administration, the nature of the formulation, the patient's size, weight, surface area, age, and sex, other drugs being administered, and the judgment of the attending clinician. Suitable dosages are in the range of 0.01-1,000 mg/kg. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The compositions can be administered shortly before or at bedtime, for example, at or within about 5, about 10, about 15, about 20, about 30, about 40, about 50, about 60 minutes, about 70 minutes, about 80 minutes, about 90 minutes of bedtime. For most subjects this is generally during the evening hours. But for those subjects who work during the night and sleep during the day, the compositions can be administered before the subject retires to bed. The duration of treatment with any composition provided herein can be any length of time from as short as one day to as long as the life span of the host (e.g., many years). For example, a compound can be administered once a week (for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly. The subject can be treated one or more times per day (e.g., once, twice, three, four, five, or six times per day) or every so-many hours (e.g., about every 2, 4, 6, 8, 12, or 24 hours). The time course of treatment may be of varying duration, e.g., for two, three, four, five, six, seven, eight, nine, ten or more days. For example, the treatment can be twice a day for three days, twice a day for seven days, twice a day for ten days.

Treatment cycles can be repeated at intervals, for example weekly, bimonthly or monthly, which are separated by periods in which no treatment is given. For example, the compositions can be administered for 1, 2, 3, 4, 5, 6, 7, 8, 9, 10, 11, 12, 13 14, 15, 16, 17, 18, 19, 20, 21 22, 23, 24, 25, 26, 27, 28, 29, or 30 or more days, followed by a period of 1, 2, 3, 4, 5, 6, 7, 8, 9, 10, 11, 12, 13, 14, 15, 16, 17, 18, 19, 20, 21 22, 23, 24, 25, 26, 27, 28, 29, or 30 or more days in which no treatment is given. The treatment can then be resumed for a period of 1, 2, 3, 4, 5, 6, 7, 8, 9, 10, 11, 12, 13, 14, 15, 16, 17, 18, 19, 20, 21 22, 23, 24, 25, 26, 27, 28, 29, or 30 or more days, followed by a second interval in which no treatment is given. The cycle of periodic administration followed by periods of no treatment can be repeated multiple times, for example, 2, 3, 4, 5, 6, 7, 8, 9, 10 or more times. The compositions can be administered daily, every 2 days, every 3 days, every 4 days, every 5 days, every 6 days, every 7 days, every 8 days, every 9 days, every 10 days, every 11 days, every 12 days, every 13 days, or every 14 days.

Any method known to those in the art can be used to determine if a particular response is induced. These can include observations from the subject's bed partner or family members reporting a reduction in snoring, or clinical assessment. The particular methods used to evaluate a response will depend upon the severity of the subject's snoring, the patient's age, and sex, other drugs being administered, the patient's perception, and the judgment of any attending clinician.

The compositions may also be administered along with another treatment for snoring, including lifestyle changes, use of oral devices or a CPAP or surgery. Concurrent administration with another method of treatment does not require that the treatment be administered at the same time as long as there is an overlap in the time period during which the treatments are exerting their therapeutic effect. Simultaneous or sequential administration is contemplated, as is administration on different days or weeks.

EXAMPLES

Example 1

Human Volunteer Study I

A composition comprising 8 mg doxylamine, 325 mg L-tryptophan, 1.5 mg melatonin was administered to an adult male subject once daily before bedtime for four consecutive days. After three days, the subject's spouse reported a complete disappearance of snoring. The subject discontinued the dosage and the snoring returned. The subject repeated the dosing protocol two additional times and again his spouse reported a cessation of snoring.

Example 2

Human Volunteer Study II

The Snoring Treatment composition was manufactured under United States Food and Drug Administration cGMP conditions. The ingredients shown in Table 1 were geometrically triturated and then equally distributed among 100 #0 Clear Locking Gelatin Capsules. The unit dose in each capsule was 8 mg doxylamine, 1.5 mg melatonin, and 300 mg L-tryptophan.

TABLE 1

Snoring Treatment Composition Manufacture

| Ingredient | Amount |
| --- | --- |
| Doxylamine Succinate USP | 800 mg |
| Melatonin | 150 mg |
| L-Tryptophan USP | 30,000 mg |

Snoring was monitored and analyzed using the SnoreLab proprietary sound wave analysis program (Reviva Softworks, Ltd) according to the supplier's directions.

The study was conducted over twenty-one consecutive nights. For the first six nights, Baseline snoring patterns were assayed. In this study, no placebo was administered because snoring—by definition—could only occur when the subject was asleep and effectively unconscious. Snoring sounds and monitoring (sleep) time were captured and analyzed using the SnoreLab software. Monitoring was started by the test subject when the subject felt drowsy, the room was quiet, and continued until a natural first awakening; when the monitoring period was terminated by the test subject. Beginning on the seventh night and for each of the following five nights (six nights total), a unit dose of the Snoring Treatment composition was administered about 30 minutes before the normal sleep time (allowing for up to 9 hours of sleep monitoring). Monitoring continued for an additional nine nights ("Recovery nights') during which no Snoring Treatment was administered.

Results:

The results of this study are summarized in Table 2. As shown in Table 2, the total Time Snoring during the monitoring period was decreased by 44% (50 minutes per night) after Snoring Treatment. The decrease in Time Snoring was sustained during the Recovery period (54 minutes per night during Recovery as opposed to 1 hour and 53 minutes during the Baseline period). The Snore Score, which is a measure of the total time the subject snored during the monitoring period combined with the snoring volume during that period, was decreased by 48% after Snoring Treatment. The decrease in the Snore Score was also sustained during the recovery period.

TABLE 2

Snoring Analysis

| | Time monitored h:m mean (std dev) | Time snoring h:m mean (std dev) | Snore Score mean |
| --- | --- | --- | --- |
| "Baseline" | 7:24 (0.04) | 1:53 (0.03) | 26.3 (11.0) |
| "Snoring Treatment" | 8:09 (0.03) | 1:03 (0.03) | 13.8 (10.2) |
| Change (%) | +10% | −44% | −48% |
| Change (h:m) | +0:45 | −0:50 | NA |
| Recovery | 7:57 (0.04) | 0:54 (0.02) | 11.5 (6.1) |

Time monitored = time between start of monitoring and stop of monitoring
Time snoring = time snoring within time monitored
h:m = hours:minutes
Snore Score = summary factor generated by SnoreLab software—combines time snoring and snoring volume
Baseline = a control baseline period without any treatment
Snoring Treatment = after taking Snoring Treatment
Recovery = after Snoring Treatment had ended
Mean = average of difference between start of monitoring and end of monitoring
std dev = Standard Deviation of the Mean A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a subject who is suffering from simple snoring, the method comprising: (a) identifying a subject who is in need of treatment for simple snoring; and (b) administering to the subject a therapeutically effective amount of pharmaceutical composition comprising an antihistamine and one or more dietary supplements.

2. The method of claim 1, wherein the composition is administered by one or more of the following routes of administration: oral, buccal, sublingual, sublabial, nasal inhalation, or transdermal.

3. The method of claim 1, wherein the composition is administered orally.

4. The method of claim 3, wherein oral administration comprises administering a capsule or tablet dosage form one or more times per day.

5. The method of claim 1, wherein the antihistamine is doxylamine, diphenhydramine, cetirizine, loratidine or fexofenadine.

6. The method of claim 5, wherein the antihistamine comprises an enantiomer of doxylamine, diphenhydramine, cetirizine, or fexofenadine.

7. The method of claim 5, wherein the anti-histamine is doxylamine.

8. The method of claim 7, wherein the therapeutically effective amount of doxylamine is from about 0.001 g to about 0.20 g per unit dose.

9. The method of claim 7, wherein the therapeutically effective amount of doxylamine is about 0.001 g, 0.005 g, 0.008 g, 0.01 g, 0.02 g, 0.03 g, 0.04 g, 0.05 g, 0.06 g, 0.07 g, 0.08 g, 0.09 g, or 0.1 g per unit dose.

10. The method of claim 1, wherein the dietary supplement comprises L-tryptophan or a metabolite thereof, 5-hydroxytryptophan or a metabolite thereof, serotonin or a metabolite thereof, N-acetyl-5-hydroxytryptamine or a metabolite thereof, or melatonin or a metabolite thereof.

11. The method of claim 10, wherein the dietary supplement is L-tryptophan or a metabolite thereof.

12. The method of claim 11, wherein the therapeutically effective amount of L-tryptophan is about 0.001 g to about 1.0 g per unit dose.

13. The method of claim 10, wherein the dietary supplement is melatonin or a metabolite thereof.

14. The method of claim 13, wherein the therapeutically effective amount of melatonin is about 0.0001 g to about 0.01 g per unit dose.

15. The method of claim 1, wherein the composition comprises doxylamine, L-tryptophan, and melatonin.

16. The method of claim 1, wherein the pharmaceutical composition comprises one or more of a vitamin, mineral, a pharmaceutically acceptable salt, or a pharmaceutical carrier.

17. The method of claim 1, wherein the composition is administered until the snoring is reduced.

18. The method of claim 17, wherein the reduction comprises a reduction in the frequency, duration or intensity of snoring.

19. The method of claim 1, wherein the composition is administered at bedtime.

20. The method of claim 19, wherein the composition is administered about 5 minutes to about 60 minutes before bedtime.

21. The method of claim 1, wherein the composition is administered at intervals separated by a period of no treatment.

22. The method of claim 21, wherein the administration is for about 2 days to about 14 days.

23. The method of claim 22, wherein the administration is for about 6 days.

24. The method of claim 21, wherein the period of no treatment is for about 3 days to about 14 days.

25. The method of claim 24, wherein the period of no treatment is for about 9 days.

26. A method of reducing simple snoring in a subject, the method comprising: a) identifying a subject in need of treatment for simple snoring; and b) administering to the subject a therapeutically effective amount of a pharmaceutical composition comprising an anti-histamine and a dietary supplement.

27. The method of claim 26, wherein the composition is administered orally.

28. The method of claim 26, wherein the antihistamine is doxylamine, diphenhydramine, cetirizine, loratidine or fexofenadine.

29. The method of claim 26, wherein the dietary supplement comprises L-tryptophan or a metabolite thereof, 5-hydroxytryptophan or a metabolite thereof, serotonin or a metabolite thereof, N-acetyl-5-hydroxytryptamine or a metabolite thereof, or melatonin or a metabolite thereof.

30. The method of claim 26, wherein the pharmaceutical composition comprises one or more of a vitamin, mineral, a pharmaceutically acceptable salt, and a pharmaceutical carrier.

31. The method of claim 26, wherein the composition comprises doxylamine, L-tryptophan, and melatonin.

* * * * *